United States Patent
Schmidt et al.

(10) Patent No.: US 10,850,011 B2
(45) Date of Patent: *Dec. 1, 2020

(54) HYDROGEL MEMBRANE FOR ADHESION PREVENTION

(71) Applicant: Board of Regents, the University of Texas System, Austin, TX (US)

(72) Inventors: Christine E. Schmidt, Gainesville, FL (US); Scott A. Zawko, Austin, TX (US); Sarah M. Mayes, Austin, TX (US)

(73) Assignee: Board of Regents, The University of Texas, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/359,102

(22) Filed: Mar. 20, 2019

(65) Prior Publication Data

US 2019/0216987 A1 Jul. 18, 2019

Related U.S. Application Data

(63) Continuation of application No. 15/597,541, filed on May 17, 2017, now Pat. No. 10,272,184, which is a continuation of application No. 14/758,873, filed as application No. PCT/US2013/074388 on Dec. 11, 2013, now Pat. No. 9,662,424.

(60) Provisional application No. 61/814,944, filed on Apr. 23, 2013, provisional application No. 61/807,629, filed on Apr. 2, 2013, provisional application No. 61/735,852, filed on Dec. 11, 2012.

(51) Int. Cl.
| | |
|---|---|
| *A61L 31/14* | (2006.01) |
| *A61F 2/00* | (2006.01) |
| *C08J 3/075* | (2006.01) |
| *C08J 5/18* | (2006.01) |
| *A61L 31/04* | (2006.01) |
| *A61L 31/16* | (2006.01) |

(52) U.S. Cl.
CPC .......... *A61L 31/145* (2013.01); *A61F 2/0077* (2013.01); *A61L 31/041* (2013.01); *A61L 31/148* (2013.01); *A61L 31/16* (2013.01); *C08J 3/075* (2013.01); *C08J 5/18* (2013.01); *A61F 2002/009* (2013.01); *C08J 2305/04* (2013.01); *C08J 2405/08* (2013.01)

(58) Field of Classification Search
CPC ........ A61L 31/041; A61L 27/26; A61L 27/52; A61L 31/145; A61L 31/148; A61L 26/0023; A61L 26/0095; C08J 2305/04; C08J 3/075; C08J 5/18; C08J 2205/022; C08J 2207/10; C08J 3/24; C08B 37/0072; C08B 37/0084; A61K 31/738; A61K 47/36

See application file for complete search history.

(56) References Cited

U.S. PATENT DOCUMENTS

| | | |
|---|---|---|
| 4,937,270 A | 6/1990 | Hamilton et al. |
| 5,017,229 A | 5/1991 | Burns et al. |
| 5,204,331 A | 4/1993 | Nishi et al. |
| 5,531,716 A | 7/1996 | Luzio |
| 5,531,735 A | 7/1996 | Thompson |
| 5,563,186 A | 10/1996 | Thompson |
| 5,760,200 A | 6/1998 | Miller et al. |
| 6,060,534 A | 5/2000 | Ronan |
| 6,096,018 A | 8/2000 | Luzio |
| 6,184,266 B1 | 2/2001 | Ronan |
| 6,294,202 B1 | 9/2001 | Burns et al. |
| 6,368,356 B1 | 4/2002 | Zhong |
| 6,372,244 B1 | 4/2002 | Antanavich |
| 6,387,978 B2 | 5/2002 | Ronan |
| 6,497,887 B1 | 12/2002 | Zecchino et al. |
| 6,521,223 B1 | 2/2003 | Calias et al. |
| 6,548,081 B2 | 4/2003 | Sadozai et al. |
| 6,629,997 B2 | 10/2003 | Mansmann |
| 6,638,917 B1 | 10/2003 | Li |
| 6,693,089 B1 | 2/2004 | Li |
| 6,723,709 B1 | 4/2004 | Pressato et al. |
| 6,818,018 B1 | 11/2004 | Sawhney |
| 6,913,765 B2 | 7/2005 | Li |
| 6,943,154 B2 | 9/2005 | Miller et al. |
| 6,960,617 B2 | 11/2005 | Omidian et al. |
| 7,265,098 B2 | 9/2007 | Miller et al. |
| 7,741,476 B2 | 6/2010 | Lebreton |
| 7,988,992 B2 | 8/2011 | Omidian et al. |
| 8,133,840 B2 | 3/2012 | Mika et al. |
| 8,668,863 B2 | 3/2014 | Zawko |

(Continued)

FOREIGN PATENT DOCUMENTS

| | | |
|---|---|---|
| CN | 102665604 | 9/2012 |
| EP | 1806367 | 7/2007 |

(Continued)

OTHER PUBLICATIONS

Na (Journal of Materials Science, online Jun. 3, 2012, vol. 23, pp. 2303-2313) (Year: 2012).*
Japan Patent Office, Notice of Reason(s) for Rejection dated Aug. 28, 2018 in Japanese Patent Application No. 2017-215179, 11 pages.
European Patent Office, Communication under Rule 71(3) EPC dated Aug. 14, 2018 in European Patent Application No. 13 863 368.0, 41 pages.
Na, et al., "Hyaluronic Acid/Mildy Crosslinked Alginate Hydrogel as an Injectable Tissue Adhesion Barrier", J Mater Sci; Mater Med (2012) 23:2303-2313, Published Jun. 3, 2012, 12 pages.
Japan Intellectual Property Office, Office Action dated May 16, 2017 in Japanese Patent Application, No. 2015-547496.

(Continued)

*Primary Examiner* — Mark V Stevens
(74) *Attorney, Agent, or Firm* — Trop, Pruner & Hu, P.C.

(57) ABSTRACT

A biocompatible membrane comprised of alginate and hyaluronate. The membrane may be used to prevent unwanted scarring after surgery. The tissue adherence and the rate of bioresorption of the membrane may be modified through an external stimulus comprising a sequestering agent and a viscosity modifier.

19 Claims, 4 Drawing Sheets

(56) References Cited

U.S. PATENT DOCUMENTS

| | | | |
|---|---|---|---|
| 8,728,499 B2* | 5/2014 | Zawko | C08L 5/10 424/400 |
| 8,927,521 B2 | 1/2015 | Jackson | |
| 8,946,194 B2* | 2/2015 | Mayes | A61K 47/36 514/62 |
| 9,095,558 B2 | 8/2015 | Mayes | |
| 9,308,069 B2 | 4/2016 | Massen | |
| 9,662,424 B2* | 5/2017 | Schmidt | A61L 31/041 |
| 10,272,184 B2* | 4/2019 | Schmidt | A61L 31/041 |
| 10,442,911 B2* | 10/2019 | Zawko | C08B 37/0015 |
| 2006/0233852 A1 | 10/2006 | Milbocker | |
| 2007/0026038 A1 | 2/2007 | Bayer | |
| 2007/0196342 A1 | 8/2007 | Sadozai | |
| 2007/0202084 A1 | 8/2007 | Sadozai et al. | |
| 2007/0270852 A1 | 11/2007 | Tormala et al. | |
| 2008/0069857 A1 | 3/2008 | Yeo | |
| 2010/0055158 A1 | 3/2010 | Vitaris | |
| 2010/0178313 A1 | 7/2010 | Larsen et al. | |
| 2010/0217403 A1 | 8/2010 | Champion | |
| 2011/0212501 A1 | 9/2011 | Yoo | |
| 2012/0039959 A1 | 2/2012 | Mayes | |
| 2012/0088735 A1* | 4/2012 | Mayes | A61K 47/36 514/54 |
| 2012/0088832 A1 | 4/2012 | Mayes | |
| 2012/0177702 A1 | 7/2012 | Altschuler et al. | |
| 2012/0282302 A1 | 11/2012 | McCanless | |
| 2013/0252921 A1 | 9/2013 | Lee et al. | |
| 2015/0010490 A1 | 1/2015 | Kim et al. | |
| 2015/0010636 A1 | 1/2015 | Delaney | |
| 2019/0216933 A1* | 7/2019 | Mayes | A61K 31/738 |

FOREIGN PATENT DOCUMENTS

| | | |
|---|---|---|
| JP | H08506364 | 7/1996 |
| JP | 2000116765 | 4/2000 |
| JP | 2003530424 A | 10/2003 |
| JP | 200441586 | 2/2004 |
| JP | 2009529926 | 8/2009 |
| JP | 2011509724 | 3/2011 |
| WO | WO 9739737 | 10/1997 |
| WO | 2008127290 | 10/2008 |
| WO | WO2010146574 | 12/2010 |
| WO | 2012024339 | 2/2012 |
| WO | WO2014093489 | 6/2014 |

OTHER PUBLICATIONS

Korean Intellectual Property Office, Notice of Preliminary Rejection (Non-Final) dated Nov. 15, 2016 in Korean application No. 10-2015-7018224.

International Searching Authority, "Notification of Transmittal of the International Search Report and the Written Opinion of the International Searching Authority," dated Sep. 12, 2014, in International application No. PCT/US2013/074388.

Mayes, Sarah, et al., "Promoting injury isolation and regeneration with a bilayer polysaccharide-polysaccharide based hydrogel film," Biologic Scaffold and Regenerative Medicine Symposium, Austin, Texas, Apr. 28, 2012.

State Intellectual Property Office, People's Republic of China, First Office Action dated Apr. 20, 2016 in Chinese Patent Application No. 201380072748.6.

European Patent Office, Extended European Search Report dated Jul. 4, 2016 in European Patent Application No. 13863368.0.

Canadian Patent Office, Examiner's Office Action dated May 6, 2016 in Canadian Patent Application No. 2894658.

IP Australia, "Patent Examination Report", dated Oct. 28, 2015 in Australian application No. 2013359344.

Indian Patent Office, First Examiner Report dated Dec. 30, 2019 in Indian Application No./ 3542/CHENP/2015, 6 pages total.

European Patent Office, Communication and Written Opinion dated Jul. 8, 2019 in European patent application No. 19 156 162.0.

Mexican Patent Office, Office Action dated Aug. 19, 2019 in Mexican patent application No. MX/a/2015/007410.

European Patent Office, Examination Report dated Jul. 29, 2020 in European patent application No. 19 156 162.0, 9 pages total.

* cited by examiner

BLOCK 605

Apply a hydrogel film to a subject, wherein the hydrogel film includes uncrosslinked hyaluronic acid and crosslinked alginate, and the alginate is crosslinked with calcium.

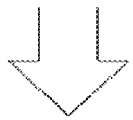

Block 607 (optional)

Apply a thickening agent to the calcium chelator to increase viscosity of the calcium chelator. This may be done before or after the calcium chelator is applied to the hydrogel (see block 610).

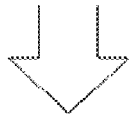

Block 610

Apply a calcium chelator to the hydrogel to (a) increase bioresorbability of the hydrogel film in response to applying the calcium chelator to the hydrogel film, (b) tune the hydrogel film's release rate for a therapeutic agent included in the hydrogel by applying the calcium chelator to the hydrogel film, and/or (c) increase the mucoadhesiveness for the hydrogel film by applying the calcium chelator to the hydrogel film.

FIGURE 6

HYDROGEL MEMBRANE FOR ADHESION PREVENTION

This application is a continuation of U.S. patent Ser. No. 15/597,541, filed May 17, 2017, and titled "Hydrogel Membrane for Adhesion Prevention", which is a continuation of U.S. patent application Ser. No. 14/758,873, filed Jul. 1, 2015, and titled "Hydrogel Membrane for Adhesion Prevention", which issued on May 30, 2017 as U.S. Pat. No. 9,662,424, which is a § 371 National Stage Entry of International Application No. PCT/US2013/074388 filed on Dec. 11, 2013, and titled "Hydrogel Membrane for Adhesion Prevention", which claims priority to: (1) U.S. Provisional Application No. 61/814,944 filed on Apr. 23, 2013, and titled "Multilayer Hydrogel", (2) U.S. Provisional Application No. 61/807,629 filed on Apr. 2, 2013, and titled "Hydrogel Based Therapeutic Agent Delivery", and (3) U.S. Provisional Application No. 61/735,852 filed on Dec. 11, 2012, and titled "Hydrogel Membrane for Adhesion Prevention". The content of each of the above applications is hereby incorporated by reference.

This invention was made with government support under Grant no. DMR0805298 awarded by the National Science Foundation. The government has certain rights in the invention.

FIELD OF EMBODIMENTS OF THE INVENTION

Embodiments of the invention relate generally to the field of medical devices and more particularly to devices that inhibit, reduce, and prevent scarring. Embodiments of the invention include a bioresorbable membrane that can be inserted into the body, between tissues and organs, to prevent unwanted scar tissue attachments.

BACKGROUND

Scar tissue attachments, also called adhesions, are a frequent complication of surgical procedures. During a surgical procedure the tissues and organs of the body may be deliberately or inadvertently injured. These injuries prompt a wound healing response that results in scarring.

Scarring is problematic when it produces scar tissue attachments between adjacent tissues and organs that should remain unattached. Adhesions are capable of forming in any anatomical location including around the eyes, tendons, heart, spinal cord, peripheral nerve, sinus, and among the organs of the abdominal and pelvic cavities. For example, a bowel resection within the abdominal cavity may lead to scar tissue attachments between the bowels and the abdominal wall. These attachments can produce pain and discomfort for the patient, impair the functioning of the effected organs, and hinder subsequent surgeries in the same anatomical region.

An anti-adhesion barrier is a medical device used by surgeons to inhibit, reduce, or prevent scar tissue attachments. These devices are commercially available as membranes, gels, and solutions. During a surgical procedure a surgeon may choose to insert an anti-adhesion barrier between injured tissues and organs. Such devices work by physically separating the injured organs during the critical period of wound healing during which patients are most at risk for adhesions. After the critical phase has passed the devices are resorbed by the body. Generally, membrane barriers are superior to gels and solutions which are resorbed by the body too quickly. Even the most successful membranes, however, are only partially effective and may suffer from brittleness and poor resorbability.

BRIEF DESCRIPTION OF THE DRAWINGS

Features and advantages of embodiments of the present invention will become apparent from the appended claims, the following detailed description of one or more example embodiments, and the corresponding figures, in which:

FIG. 6 includes a method 600 in an embodiment of the invention.

DETAILED DESCRIPTION

Figure 1:
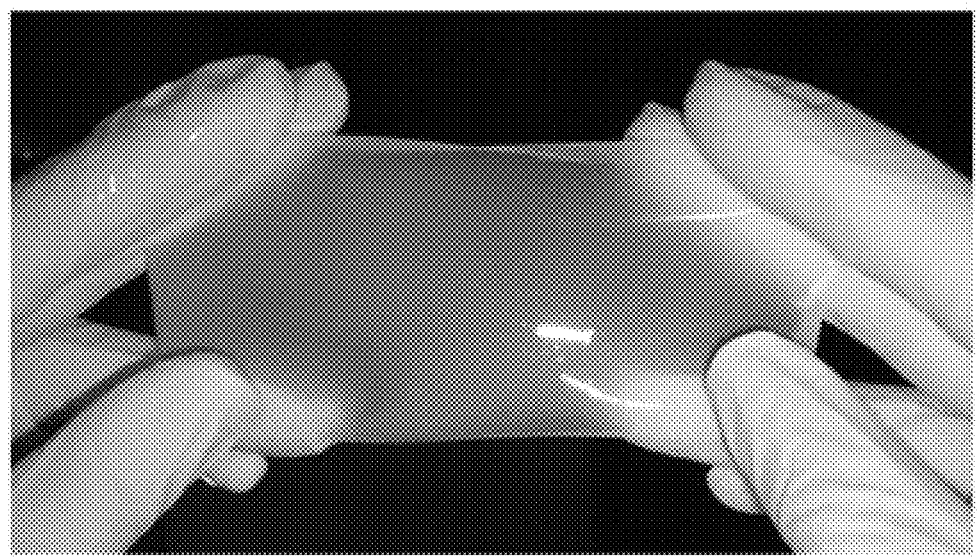
FIG. 1 includes a photo of a hydrogel in an embodiment of the invention.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Clinicians are seeking anti-adhesion membranes with improved handling properties and greater efficacy. As discussed below, various embodiments of the invention provide a membrane that is hydrated, resorbable, and effective.

An embodiment includes a membrane comprised of two polysaccharides: alginate and hyaluronate. An embodiment may include a membrane including only alginate and hyaluronate and little to nothing else. The proportions of each polymer within the membrane may vary with different embodiments For example, in one embodiment the alginate component may constitute up to 95%, and no less than 10%, of the dry mass (with hyaluronate constituting the remaining portion of the film). In another embodiment the membranes comprise no more than 75% and no less than 50% alginate by dry weight (with hyaluronate constituting the remaining portion of the film). In an embodiment the membranes comprise between 60% and 70% alginate (with hyaluronate constituting the remaining portion of the film).

In an embodiment the alginate component may be a copolymer of mannuronate (M) units and guluronate (G) chemical units. The alginate backbone may consist of these two units arranged in repeating blocks and alternating blocks (e.g., MMMMMM, GGGGGG, and MGMGMG patterns).

The proportion of M and G units in a particular alginate is dependent on, for example, the plant source from which the alginate is harvested in some embodiments. Alginates may be characterized by the proportion of M and G units. The alginate component in an embodiment may be any type of alginate including alginates with a high proportion of M units (i.e., high-M alginate), alginates with a high proportion of G units (i.e., high-G alginate) and blends of high-M and high-G alginates. In an embodiment a "high proportion" of a unit constitutes more than 50% but in other embodiments the value may be 60%, 70%, 80%, 90%, or higher.

Alginates may be obtained in a variety of salt forms. The alginate salts of alkali metals (e.g., sodium and potassium) and magnesium are water soluble. The alginate salts of alkaline earth metals (e.g., calcium, strontium, barium) are water insoluble. Alginate can also form insoluble salts with transition metals such as iron and copper. The water insolubility of alginate salts may be due to ionic crosslinking by multivalent cations of the G-units in alginate's backbone. In an embodiment a water soluble alginate is used to prepare solutions for film casting. After casting the alginate is converted to an insoluble salt form by ion exchange to obtain the final membrane. In an embodiment sodium alginate is used for film casting and subsequently converted to calcium alginate after the membrane has been obtained. Calcium, an element found throughout the body, may serve as a crosslinker and is a suitable option from the point of view of biocompatibility.

Hyaluronate is an alternating polysaccharide of N-acetyl-glucosamine and glucuronic acid chemical units. The polymer can be obtained from, in various embodiments, both animal and bacterial sources and in a number of molecular weights. An acid form, hyaluronic acid (HA), can be obtained but has limited water solubility. Hyaluronate stocks for research and clinical use are predominantly salts, particularly sodium salts. In an embodiment sodium hyaluronate salt is used for membrane preparation due to, for example, its commercial availability. Other salts can also be obtained, but unlike alginate, these salts are water soluble.

Hyaluronate is found throughout the connective tissues of the body particularly in the skin, cartilage, and vitreous fluid of the eye. It is an unusually large macromolecule that can reach molecular weights of up to several million. It is capable of binding to specialized proteins to form macromolecular complexes that are structural frameworks for tissue development and wound healing. The backbone of hyaluronate is highly negatively charged due to the prevalence of carboxyl functionalities. Hyaluronate is unique in the body due to the combination of high molecular weight and high charge density. These properties may make hyaluronate capable of binding to many water molecules thereby helping tissues to maintain hydration and homeostasis.

Hyaluronate is biocompatible. Hyaluronate is nearly ubiquitous throughout the tissues of the body; therefore, the immune system does not recognize it as foreign. Additionally, hyaluronate is strongly associated with wound healing and particularly with scar-free wound healing and fetal tissue development.

HA may be crosslinked. Methacrylate groups are bound to an available carboxylic acid group and these groups then bind together via photocuring. However, photocrosslinked HA alone renders films that may not be robust, may tear easily, and may be difficult to handle. In order to obtain films that have more structure and strength, an embodiment adds alginate. Calcium is used as a crosslinker because it is biocompatible and the body has systems in place to regulate calcium levels.

More specifically, an embodiment includes a membrane comprised of both hyaluronate and alginate. In addition to these polymers the membranes may also contain a significant proportion of water and can be classified as hydrogels. Hydrogels are materials that swell when exposed to excess water. At a molecular level hydrogels are comprised of a network of polymer chains that are dispersed within an aqueous medium. A feature of the hydrogel membranes of an embodiment is the crosslinks that tie together the individual polymer chains. These crosslinks allow the hydrogel to swell in water but prevent it from completely dissolving. Hydrogels tend to be biocompatible because water itself is biocompatible. Hydrogels therefore are attractive for clinical applications in which materials will come into close contact with living tissues.

In an embodiment alginate forms the framework of the membrane due to its ability to create crosslinked gels in the presence of calcium. This crosslinked framework provides mechanical stability and shape to the membrane. The hyaluronate component is entrapped within the alginate gel and its release is limited by its large size compared to the pores of the alginate gel. Hyaluronate is more hydrophilic than alginate and therefore hydrogel compositions with greater proportions of hyaluronate exhibit greater water swelling. When the ratio of hyaluronate to alginate is low the hyaluronate component is entirely or partially entrapped within the crosslinked alginate matrix and leaching is limited; but when the ratio of hyaluronate to alginate is high, the crosslinked alginate may be unable to retain the leachable hyaluronate component. The hyaluronate component can be leached by rinsing the membrane in water for which hyaluronate has a strong affinity. When hyaluronate is leached it leaves behind empty pores within the membrane that provide an interconnected pathway for diffusion of water. By altering the pores, and therefore the water content of the membrane, the physical properties of the membrane such as flexibility and elasticity are also altered. The leaching of hyaluronate from the membrane during manufacturing may be used as a means to advantageously modify the physical properties of the membrane. The leaching of hyaluronate may also occur in vivo as a means to deliver hyaluronate to a wound site to capitalize on hyaluronate's pro-regenerative wound healing properties.

Figure 2:
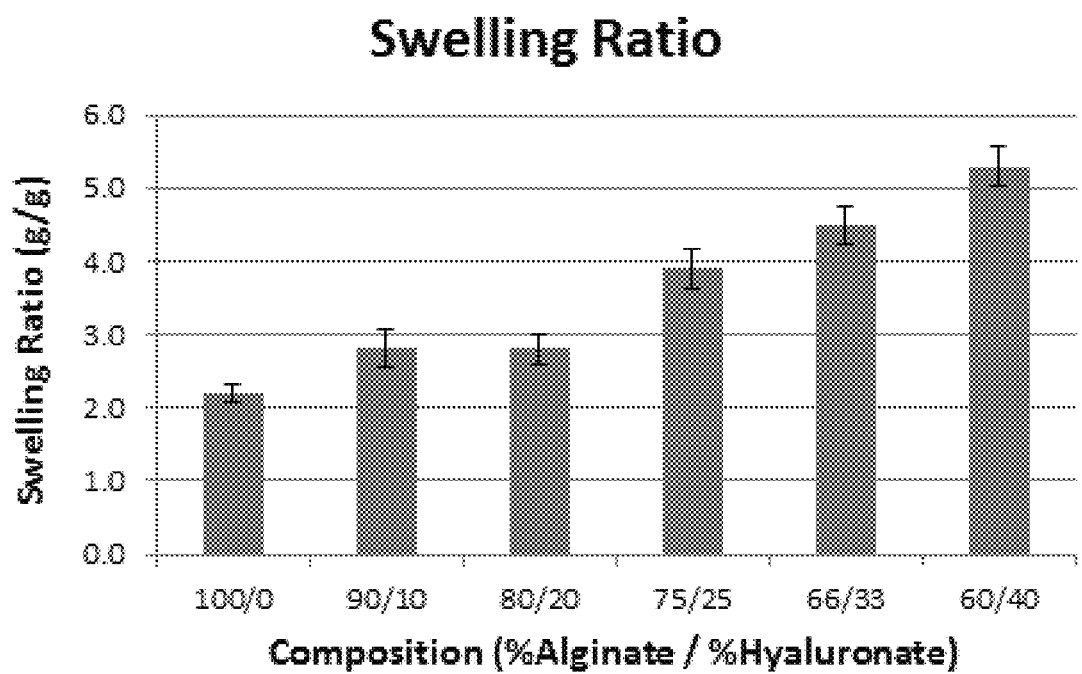
FIG. 2 includes a chart regarding swelling of a hydrogel in an embodiment of the invention.

FIG. 2 shows the water swelling ratio of alginate/hyaluronate membranes as a function of composition. The membranes are hydrophilic and absorb water. Increasing the proportion of hyaluronate within the membranes renders them more hydrophilic and increases their water swelling capacity.

In an embodiment membranes are prepared through solution casting. This requires dissolving water soluble salt forms of the alginate and hyaluronate in an aqueous mixture. Then a volume of the solution can be dispensed into a mold. A suitable mold can be of any shape or size. The water from the solution may be evaporated to obtain a dry thin film which can be crosslinked by a soak in an aqueous solution of a calcium salt. Crosslinking produces a hydrogel membrane that swells in water but does not dissolve. Similar techniques for obtaining cast films such as spin-casting, doctor-blading with a casting knife, extrusion and the like can produce films without the need for a water evaporation step. These films can be crosslinked with calcium without the need for drying.

A doctor blade is a tool used to create wet films with a defined thickness. To use the doctor blade in an embodiment one dispenses a volume of alginate/hyaluronate solution onto a substrate. Then one pulls the doctor blade over the solution to spread it into a flat film of defined thickness. The doctor blade removes excess solution thereby producing a wet film of predefined thickness coating the substrate.

Tissue Anchor

Discussion now turns more specifically to an embodiment for a liquid tissue anchor with a sequestering solution. Embodiments of the tissue anchor described below may be used with embodiments discussed above or may be used independently of those embodiments.

An embodiment includes a method of treating an adhesion barrier, or any implantable device, comprised of crosslinked constituents (such as calcium alginate) that can be uncrosslinked by removing one or more crosslinking agents (such as calcium), with a sequestering solution that removes the crosslinking agent(s) (such as calcium) at the site of injury. An embodiment of the invention can also be understood as the sequestering solution itself (independently of the implant).

One embodiment of a sequestering solution includes a calcium chelator, but other embodiments are not so limited.

In an embodiment the sequestering solution works by disrupting the crosslinks (see discussion above regarding crosslinking embodiments) within the implant. Disruption of the crosslinks occurs by bonding of the sequestering agent to the crosslinking agent within the implant. For disruption to occur, in one embodiment the sequestering agent bonds more strongly to the crosslinking agent than does the crosslinkable component of the implant. More specifically, a sequestering agent is able to sequester the crosslinking agent or ion because by doing so, the overall energy of the system is lowered. This energy lowering causes a relaxation of the implanted device, reducing the mechanical integrity of the device. The device conforms to the tissue geometry, and becomes mucoadhesive by nature of hydrogen bonding. This mucoadhesivity removes the need for other anchoring devices such as sutures or tissue glue.

Figure 3:
FIG. 3 includes a series of photos illustrating mucoadhesiveness of an embodiment of the invention.

FIG. 3 is a sequence of photos depicting the application of a membrane of alginate and hyaluronate to the intestine of a rat model of abdominal injury. The membrane is flexible and easy to position at the correct site. The syringe applies an optional liquid tissue anchor that promotes tissue adherence and bioresorption of the membrane.

Mechanically robust implants (such as an alginate adhesion membrane) may persist inside the body beyond the critical healing period (about two weeks), which may be problematic because the odds of an undesirable immune response are greater if the implant persists within the body for a long period of time. However, in an embodiment the sequestering solution increases the rate of bioresorption of the adhesion barrier. In an embodiment the implanted device completely resorbs within two weeks postsurgically, based on its use with the sequestering solution. However, other embodiments may shorten or lengthen this period of time.

In various embodiments suitable sequestering agents are salts of organic molecules that have multiple anionic functional groups capable of bonding to a crosslinking agent (such as calcium, magnesium, cadmium, silver, zinc, silicon, oxidants, protic acids, compounds that can be metallated). Examples are the salts of citric acid, EDTA, EGTA, BAPTA, tetracycline, and phosphates.

In an embodiment the strength of the sequestering solution is dependent on the molar concentration of the sequestering agent. For example, a solution formulated with a greater molar concentration of sequestering agent disrupts a greater number of crosslinks within the implant and accordingly increases the rate of bioresorption. Therefore, the concentration of the sequestering agent within the sequestering solution can be tuned to obtain a desired rate of implant resorption within the body. For example, 300 mM citrate yields a 1 week bioresorption of an alginate/hyaluronate film crosslinked with 100 mM calcium chloride solution. Meanwhile 100 mM citrate yields a 2 week bioresorption of an alginate/hyaluronate film crosslinked with 100 mM calcium chloride solution. Furthermore, without use of the sequestering solution, this same film persists for 6 weeks. This tunability allows for one implant to facilitate healing support for various indications. For example, hernia repair may require longer time periods of support until fibroblast ingrowth is sufficient, like 6 weeks. This timeframe is opposed to abdominal adhesion prevention which requires bioresorption in about 2 weeks.

In an embodiment a surgeon uses the sequestering solution during any surgical procedure in which an implant, comprised of crosslinked constituents (such as calcium alginate) that can be uncrosslinked with the sequestering solution, is used to prevent unwanted tissue adhesions or unwanted scar tissue attachments. The surgeon applies the sequestering solution by a suitable delivery device (e.g., syringe, spray, and the like) to the surface of the implant. The sequestering solution acts quickly to disrupt the unwanted crosslinks (such as calcium). The treated implant then conforms to and adheres more strongly to the contours of the underlying tissues.

To facilitate application of the sequestering solution to the injury site, in an embodiment the sequestering solution may be formulated with a thickening agent. The thickening agent increases the solution viscosity to produce a thick, syrupy liquid. A beneficial effect of the thickening agent is that the more viscous sequestering solution is better confined to the site of application than is a less viscous watery solution. An embodiment includes a thickening agent such as sodium hyaluronate, which is known for both its biocompatibility and solution thickening properties.

In the interests of biocompatibility in various embodiments the sequestering solution can be formulated with salts to buffer the pH or adjust the osmolarity such as those found in commonly used phosphate buffer solution.

An embodiment includes an alginate barrier crosslinked specifically with calcium and treated with a corresponding calcium sequestering solution. However, in other embodiments the same method can be applied to other ions as well. For example, in various embodiments alginate barriers are crosslinked with cations such as barium, strontium, copper, iron, and the like. The same sequestering agents may be used to disrupt these crosslinking agents.

Crosslinking of materials includes an increase in the number of bonds between a material and itself or other materials. An increase in bonds causes a change in the refractive index of the overall material, distorting light going through the material. As the embodiment includes a sequestering solution that decreases the bonds in an implant, the refractive index of the resulting implant will be changed upon administration of the sequestering solution. For example, an alginate and HA adhesion barrier is translucent when crosslinked, and transparent after a calcium sequestering solution is applied. FIG. 1 shows an example of membrane, 2 cm×4 cm, comprised of alginate and hyaluronate. The membrane is thin, flexible, hydrophilic, translucent, and has slick, lubricious surfaces.

In an embodiment, the hydrogel membrane and the sequestering solution may be provided within a kit. The kit would also include a delivery device suited for applying the sequestering solution to the wound site. A surgeon or other health care provider in an operating room setting would use the kit to apply the membrane and appropriate volume of sequestering solution to the wound site. This approach would afford the end user great flexibility to adjust the membrane size and solution volume to meet patient specific needs.

The sequestering solution may be applied to the membrane hours, days, or weeks after the membrane's implantation. For example, the hydrogel membrane may be placed at a wound site (e.g., flexor tendon repair) for the prevention of unwanted scar tissue attachments. After the time period for scar formation has passed, generally 3 to 14 days, the membrane barrier is no longer needed; therefore, the sequestering solution may be injected into the wound site to completely solubilize the membrane. This action would have as its purpose elimination of the membrane from the wound site thus precluding an unwanted foreign body response. The sequestering solution can be introduced by a needle and syringe penetrating through the surrounding tissue or can be introduced by minimally invasive surgical means.

Multilayer Hydrogel

One embodiment of the invention includes a polysaccharide-based bilayer hydrogel film that promotes regeneration in one layer and prevents unwanted scar tissue formation in a second layer. Hydrogels, such as those described in WO2009/108760, WO2012/048283, WO2012/048289, are used to form a multi-layer hydrogel with distinct layers that provides a regenerative effect in one layer, and an anti-adhesive effect in a second layer. The hydrogel regenerative layer promotes cell attachment and proliferation in vitro. The hydrogel anti-adhesive layer prevents unwanted cell attachment and limits fibrotic tissue formation. Hydrogels can be rolled into a conduit with either the anti-adhesive or the regenerative side exposed to the lumen.

An embodiment includes a bilayer hydrogel composed of biopolymers that prevent scar tissue attachment on one side, and encourage healthy regeneration on the other side. The anti-adhesive layer is comprised of hyaluronic acid and alginate. The regenerative layer is comprised of collagen and hyaluronic acid. The two layers are distinct and are covalently bound. An embodiment includes a collagen matrix that encourages cell attachment and proliferation.

Embodiments solve the problems of unwanted soft tissue attachments as well as decreasing critical healing time by supporting regeneration of injured tissues. Various embodiments provide anti-adhesive and regenerative layers using nonsynthetic, all-natural components. An embodiment includes a biocompatible, bilayer hydrogel composed of naturally occurring polysaccharides.

An embodiment is self-adherent and does not require sutures or screws. An embodiment may be coupled (e.g., coated with) a mesh material to allow for better tissue coupling (e.g., suturing tissue to the mesh) and may be useful in various procedures such as hernia repair, cholecystectomy, and the like. More generally, embodiments may be implanted in various surgeries including surgeries in the peritoneal cavity and/or procedures relating to abdominal, gynecological, lung, tendon, cardiac, nerve anatomy and the like.

In one embodiment membranes of alginate and a photoreactive derivative of hyaluronic acid (GMHA) were prepared according to methods such as those described in WO2009/108760, WO2012/048283, WO2012/048289, all of which are hereby incorporated by reference. After preparation of the first membrane layer, the sample was dried under sterile conditions and a second layer of collagen and GMHA was cast on top. The two layers were chemically crosslinked and fused by treatment with 1-ethyl-3-(3-dimethylaminopropyl) carbodiimide (EDC). Bilayer formation was confirmed using confocal images of fluorescently labeled hyaluronic acid and immunostained collagen. In vitro cell morphology was characterized using diamidino-2-phenylindole (DAPI). In vitro cell morphology and characterization indicate that the collagen layer effectively provides an adhesive, proliferative substrate. The anti-adhesive layer effectively prevents cell proliferation and attachment.

Figure 4:
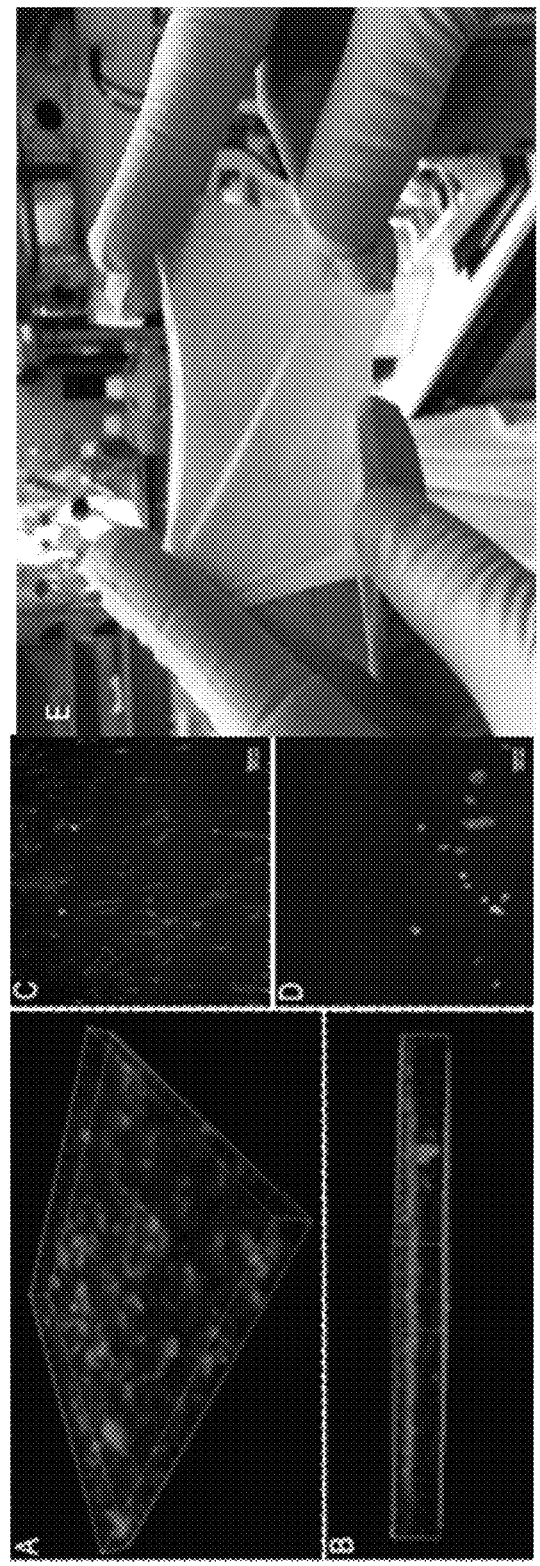
FIG. 4 addresses a bilayer hydrogel in an embodiment of the invention.

FIG. 4 includes images of a bilayer film comprising alginate, hyaluronate, and collagen. This film was imaged by confocal laser scanning fluorescence microscopy. FIGS. 4(A) and 4(B) depict the presence of fluorescently labeled hyaluronic acid in the anti-adhesive layer (comprising hyaluronate and alginate) and the regenerative layer (comprising hyaluronate and collagen), respectively. FIG. 4(C) shows the adherent morphology of human dermal fibroblast cells attached to the regenerative layer. FIG. 4(D) shows the cells are poorly attached to the anti-adhesive layer. FIG. 4(E) is a photograph depicting the advantageous handling properties of the bilayer film. Altogether, these images indicate that the regenerative layer provides an adhesive substrate for cells and the anti-adhesive layer effectively prevents cellular attachment.

Figure 5:
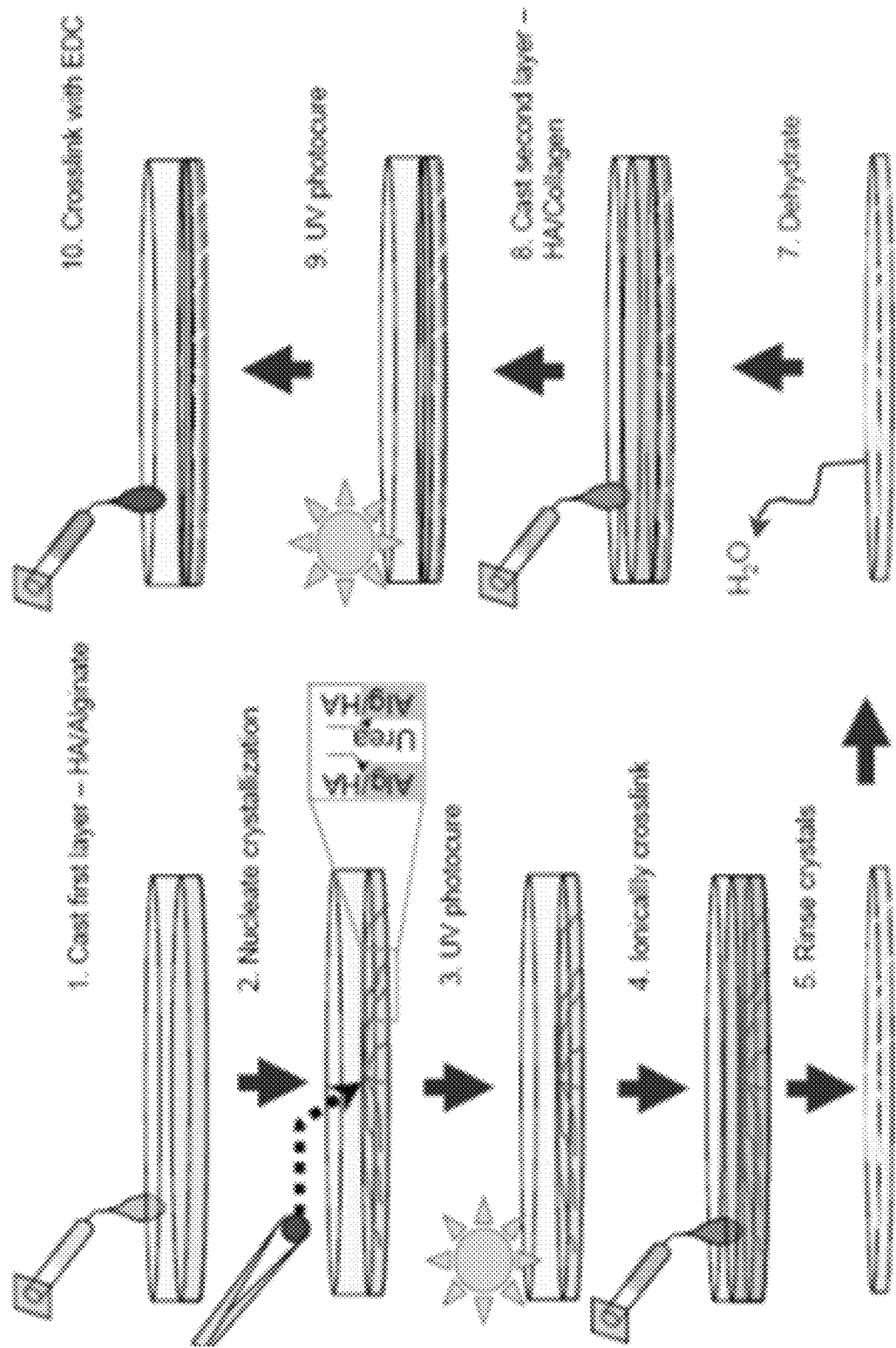
FIG. 5 includes a process for making a bilayer hydrogel in an embodiment of the invention.

In FIG. 5 HA is a linear polysaccharide with repeating disaccharide units composed of sodium D-glucuronate and N-acetyl-D-glucosamine. This naturally occurring glycosaminoglycan is a component of skin, synovial fluid, and subcutaneous and interstitial tissues. HA is metabolically eliminated from the body, and plays a role in protecting and lubrucating cells and maintaining the structural integrity of tissues. Anionic carboxylic groups immobilize water molecules giving HA its viscoelastic and anti cell-adhesive properties. In various embodiments, the layers can be fused together using any suitable crosslinking technique. For example, photoinitiated crosslinking of the film's components, grafted with polymerizable functionalities, will fuse the layers. Suitable chemical crosslinkers, such as EDC, may also be used. Ionic crosslinking, such as calcium crosslinking of alginate components, can also fuse together the various layers. One can see surgical field even with addition of second layer.

While FIG. 5 includes crystal templating another embodiment may involve the same process however the embodiment omits crystal templating related steps (e.g., steps 2 and 5 are not practiced in an embodiment but the remaining steps of FIG. 5 are practiced) and instead proceeds with an antiadhesive layer consisting essentially of HA and alginate.

While bilayer hydrogels have been repeatedly discussed embodiments are not limited to two layers and may instead include 3, 4, 5, 6, 7, 8 or more layers. Outer layers may both be anti-adhesive with one or more proregenerative layers located between the outer layers.

Also, embodiments are not restricted to HA/collagen and alginate/HA layers. For example, the anti-adhesive layer may be composed of any polymer or combinations of polymers that present a lubricious non-adhesive surface. The regenerative layer may be composed of any combination of polymer or protein (e g, laminin) that promotes cellular attachment and proliferation.

Therapeutic Agent Delivery

An embodiment of the invention includes a biocompatible membrane comprised of alginate and hyaluronate that releases a pharmaceutically active ingredient at a wound site. The active ingredient may be an antibiotic, anti-inflammatory, chemotherapeutic, anti-scarring, and/or proregenerative drug such as a growth factor or stem cell.

Scarring, inflammation, and bacterial infection are unwanted complications of surgical procedures. During a surgical procedure the tissues and organs of the body may be deliberately or inadvertently injured. These injuries may prompt a wound healing response that results in scarring and inflammation. Scarring may be problematic when it produces scar tissue attachments between adjacent tissues and organs that should remain unattached. A patient may be prone to bacterial infection particularly around polymeric or metal implants that provide niches for bacterial growth.

An embodiment includes a membrane, comprising alginate and hyaluronate, with an entrapped pharmaceutically active ingredient. An embodiment is comprised essentially of alginate and hyaluronate, with an entrapped pharmaceutically active ingredient. In an embodiment a drug-loaded membrane is obtained by mixing alginate and hyaluronate with the active ingredient, either in a dispersed or microcrystalline form, in solution and then using a method, such as casting into a mold, spin-coating, doctor blading, and the like to obtain a planar membrane. The membranes may then be stabilized through crosslinking with multivalent cations, such as calcium (but not limited to calcium). Optionally, the membranes may be further stabilized by substituting either alginate or hyaluronate with photo-reactive derivatives thereof that undergo chemical crosslinking when triggered by ultraviolet or visible light sources. In an embodiment membranes may be prepared without the active ingredient and then subsequently loaded with the ingredient. For example, a membrane may be dipped into a concentrated solution thus allowing the membrane to absorb the active ingredient from the solution. In an embodiment the membrane may be incubated with a solution of an active ingredient that becomes covalently or electrostatically bound to the polymers comprising the membrane.

An embodiment includes a method for using one of the aforementioned drug-loaded membrane embodiments to inhibit, reduce, or prevent scarring, inflammation, or bacterial infection. The membrane may be used in any anatomical location of the body following a surgical procedure for which there is a risk of unwanted scarring or inflammation. For example, the abdominal cavity, peritendinous space, sinus cavity, and the like. Likewise, the membrane may be placed near or around any implant that poses a risk for bacterial infection. An embodiment includes a method for using an aforementioned drug-loaded membrane embodiment to deliver a chemotherapeutic to a tumor or to a surgical site following tumor resection. In an embodiment the invention is a method for using an aforementioned drug-loaded membrane embodiment to deliver pro-regenerative agents, such as growth factors and stem cells, to enhance tissue repair and healing. A membrane may be used in both open and minimally invasive surgical procedures.

An embodiment includes a method of treating a drug-loaded membrane with a stimulus, preferably a solution or gel, to modify the release properties of the membrane. For example, the solution may increase the rate of membrane dissolution thus increasing the rate of release of the entrapped pharmaceutically active ingredients. Such a solution includes a chelator that sequesters the multivalent cations stabilizing the membrane. In an embodiment a solution is comprised essentially of a chelator that sequesters the multivalent cations stabilizing the membrane. The solution may be applied following placement of the membrane onto a wound or into a surgical site. However, in another embodiment the solution may be applied to the membrane hours, days, or weeks after the membrane's implantation. By applying the solution at a later point in time a medical care provider will be capable of tailoring the drug release to match the particular needs of the patient.

An embodiment includes a membrane that targets release of the active ingredient to the wound site so the side-effects of systemic delivery can be avoided. Such an embodiment is biocompatible and bioresorbable. Embodiments including membranes may be easily cut and trimmed during a surgical procedure and are convenient for covering the wounded surfaces of tissues and organs. Such embodiments may be inserted into a deep or superficial wound to release an active ingredient that will reduce or prevent scarring, inflammation, or bacterial infection.

The hydrogel membrane is comprised of a network of alginate and hyaluronate that is swelled in water. This network provides pores that can absorb an active ingredient from a concentrated solution. The pores of the hydrogel membrane comprise interconnected pathways through which water can permeate. Initially, the pores are small, in the range of angstroms to nanometers, and can accommodate only small molecules such as solvents, salts, and organic metabolites. Permeation of the membrane with water swells the pores thereby increasing their size and volume. The fully swelled pores, in the range of nanometers to micrometers, can accommodate the diffusion of peptides, proteins, and macromolecules.

The pores of the membrane may also be formed by the leaching of the membrane's hyaluronate component. When the ratio of hyaluronate to alginate is low the hyaluronate component is entirely or partially entrapped within the crosslinked alginate matrix and leaching is limited; but when the ratio of hyaluronate to alginate is high, the crosslinked alginate may be unable to retain the leachable hyaluronate component. The hyaluronate component can be leached by rinsing the membrane in water for which hyaluronate has a strong affinity. When hyaluronate is leached it leaves behind empty pores within the membrane that provide an interconnected pathway for diffusion of water and drug molecules. The leaching of hyaluronate from the membrane may occur in vivo and be used as a method to deliver hyaluronate to a wound site. This may be advantageous as a method to capitalize on hyaluronate's pro-regenerative wound healing properties.

In an embodiment, the membranes can be prepared with an interconnected network of pores, on the scale of micrometers to hundreds of micrometers, through crystal templating. Crystal templating is a method in which nucleation and growth of crystals within a cast film creates a porous network. Such a membrane could be prepared by casting a solution of alginate, hyaluronate, and a crystallizable molecule into a form or vessel; allowing the solvent to evaporate; growing crystals of the crystallizable molecule through spontaneous nucleation or deliberate introduction of a seed; crosslinking the alginate and/or hyaluronate around the crystals; and dissolving the crystals such that a pore network in the shape of the crystals has been templated into the membrane. The process of crystal growth ensures the interconnectivity of the pores and can yield dendritic architectures. This pores-based architecture has advantageous affects on the diffusion and release of entrapped drug molecules (e.g., continuous pores allow for greater diffusion of drugs into the hydrogel).

Solutions from which the membranes may absorb drugs or other therapeutic agents may be aqueous solutions because water is a good solvent for both swelling of the hydrogel membrane and facilitating the diffusion of active ingredient into the pores. However, many drugs have poor solubility in water; therefore, the concentrated solutions may also be mixed solutions comprising water and a water-miscible solvent, such as an alcohol (e.g., methanol, ethanol, ethylene glycol, and the like), a water-miscible polar aprotic solvent (e.g., acetone, dimethyl sulfoxide, dimethylformamide, and the like), an acid, and/or base. These mixed solutions have the benefit of both dissolving drugs that are poorly water soluble and for swelling the membrane. The proportion of water in these mixtures may range from 100% to 0% to suit the solubility properties of a particular drug.

The hydrogel membrane is not limited to the type of drug which it may incorporate. In various embodiments the hydrogel membrane may incorporate proteins, peptides, and small molecules. Embodiments may include chemotherapeutics, pro-regenerative drugs such as growth factors and stem cells, and drugs used for the prophylaxis or treatment of inflammation, infection, scarring, and adhesion. Embodiments may comprise an active ingredient selected from vancomycin, tobramycin, doxorubicin, mometasone furoate, and their hydrochloride salts. In an embodiment the hydrogel membrane may also be formulated to release macromolecules such as vascular endothelial growth factor and sodium hyaluronate. The hydrogel membrane may be formulated with non-active ingredients, such as binders, surfactants, salts, and the like to support the release of the active ingredient.

The drug-loaded hydrogel membrane may be used during surgical procedures. In one embodiment the drug-loaded membrane may be placed on top of wounded tissues and organs to reduce scarring and inflammation. The wounded tissues may be either internal, in which case the membrane would be inserted into a body cavity, or external, in which case the membrane would be applied topically over the wounded area. In an embodiment, the drug-loaded membrane may be placed adjacent to implants that are at risk for introducing a bacterial infection into the surgical site. In an embodiment, the drug-loaded membrane may be placed near a tumor or at the site of a tumor resection to release a chemotherapeutic.

In an embodiment, the hydrogel membrane, initially unloaded with drug, may be provided within a kit that includes a drug component that is to be combined with the membrane just prior to use. This approach may be advantageous by allowing separate storage conditions for the membrane and drug. For example, a surgeon, nurse, or other health care practitioner in a hospital, office, or operating room setting may open the kit, dip the membrane into the drug solution, and then apply the drug-soaked membrane to an injury site. This approach would afford the end user great flexibility to mix and match membrane and drug combinations to meet patient specific needs based on disease state, body weight, age, and metabolism.

The timing of the release of drugs from the hydrogel membrane is determined by a number of factors. Among these factors are the amount of drug loaded, the membrane composition (e.g., ratio of hyaluronate to alginate), the extent of crosslinking, and the water content of the membrane. For example, increasing the ratio of hyaluronate to alginate may decrease the crosslink density of the membrane thereby increasing the permeability of the membrane to diffusion of encapsulated drug. As another example, membranes with greater water content may exhibit faster release because water content through swelling is correlated to membrane porosity.

In an embodiment the release of active ingredient from the membrane may be modified by the use of a stimulus. Such a stimulus, in the form of an aqueous solution or gel, comprises a chelator that sequesters the crosslinking ions (e.g., calcium) that stabilize the membrane. In an embodiment such a stimulus, in the form of an aqueous solution or gel, may be comprised essentially of a chelator that sequesters the crosslinking ions (e.g., calcium) that stabilize the membrane. Suitable chelators are salts of organic molecules that have multiple anionic functional groups capable of bonding to calcium (or whatever crosslinking ion was used). Examples are the salts of citric acid, EDTA, EGTA, BAPTA, tetracycline, and phosphates. The stimulus may be applied during surgical procedures following insertion of the membrane into a person's body. In response to the stimulus the membrane swells, increasing the pore size of the membrane, and increasing the rate of diffusion of active ingredient from the membrane into the wound environment. The pore size may be increased by at least a factor of 10 and up to a factor of 1,000 or more. The beneficial effect of the stimulus is that the rate of drug release may be tailored to match a patient with respect to body weight, age, metabolism, or disease state. The stimulus may be delivered via syringe, spray mechanism, or the like, to the surface of the implanted membrane.

In another embodiment the stimulus may be applied to the membrane hours, days, or weeks after the membrane's implantation. For example, a hypothetical membrane loaded with vancomycin, an antibiotic, may be inserted adjacent to a bone implant. This membrane will exhibit a release of antibiotic. If a health care provider recognizes symptoms of infection around the bone implant they may choose to stimulate the membrane to increase the release rate of this antibiotic to combat the infection. After the entirety of drug has been released the health care provider may decide that the membrane, having served its purpose of vancomycin delivery, should be completely solubilized through the action of the stimulus thus eliminating the presence of the foreign membrane from the wound site. The stimulus can be introduced by a needle and syringe penetrating through the surrounding tissue or can be introduced by minimally invasive surgical means.

Many of the aforementioned embodiments combine a therapeutic agent with a porous hydrogel. One such porous hydrogel mentioned concerned a crystal template hydrogel. As one example, the embodiments found in U.S. Pat. Appl. Pub. No. US20110008442 may be utilized with therapeutics. The application, the contents of which are hereby incorporated within, includes some embodiments having hydrogels with pores formed via crystal templating and other embodiments having pores formed without crystal templating. The therapeutic agents described herein may be included these pores of any of these embodiments.

An embodiment includes a tissue anchor that may be used to deploy therapeutic agent. For example, a hydrogel including a therapeutic agent may be applied to an agent. The hydrogel may be applied to the patient and left alone. However, a stimulus may be used to "tune" the hydrogel.

For example, a hydrogel may include calcium crosslinking and a therapeutic agent. A calcium chelator may be applied to the calcium crosslinked hydrogel to (1) help the hydrogel adhere to the patient (e.g., adhere to a tumor), (2) promote or tune the dissolution time for the hydrogel (e.g., 1 hour or 1 week), and (3) tune the therapeutic agent application time (e.g., 1 hour or 2 weeks).

Embodiments may be combined with multilayer hydrogels described above. Thus, an embodiment includes a multilayer hydrogel that may be used to deploy therapeutic agent. The multilayer hydrogel may include a first layer that provides a regenerative effect (e.g., a regenerative layer including collagen and hyaluronic acid), and a second layer that is anti-adhesive (e.g., an anti-adhesive layer including hyaluronic acid and alginate) and further includes a therapeutic agent with the pores of the second layer.

An embodiment includes a film with four factors that may be beneficial for an adhesion barrier. Embodiments solve a traditional burden with adhesion barriers—poor handling characteristics. This has prevented strong market acceptance of barriers. Regarding the four factors, the first factor includes the ability for the barrier to be manipulated in ways relevant to a surgical setting (e.g., open surgery, using a trocar for laparoscopic delivery, and the like). The second attribute is tissue adherence. If the barrier can remain in place where it is implanted, then it not only provides a site specific tissue support but also eliminates (or at least reduces) the requirement for sutures or another fixing step. The third attribute is conformability. The last attribute is bioresorbability. An embodiment of the invention meets all four of these factors.

An embodiment uses a technique for adding porosity and fibers to a hydrogel. There is flexibility to use different crystals, different densities of biopolymer to make for a process that is easily adjustable, gives different polymer properties, different patterns, and the like. In addition to this flexibility is the ability to scale up production of the hydrogels. An embodiment includes photocrosslinking HA around the crystalline network and then further chemically crosslinking the alginate around the crystalline network. Compression of the biopolymers into fiber-like structures reinforces the strength of the film while the porous network gives rise to elasticity. Thus, the crystallization process imparts unique fibers and pores that provide required handling properties in otherwise brittle materials. The crystallization process is inexpensive, simple, not time consuming, and does not require sophisticated equipment or skills. Film casting is not different from any other casting.

An embodiment may be applied wet, which lends itself to endoscopic procedures and removes the need to dessicate the surgical field. The film is flexible and is translucent to allow a view of the surgical field. Also, a surgical incision can be much smaller than the wetted implant. An embodiment of the film is also repositionable for a time. For example, with one embodiment upon initial placement within the surgical field the films are easily repositionable. However, within 24 hours of placement the films undergo a gel-to-mucinous transformation. At this point the films are no longer repositionable and are strongly adhered to the tissue. This transformation is caused by displacement of calcium crosslinks within the films by endogenous sodium ions.

An embodiment of the invention includes a membrane comprising alginate and hyaluronate. The membrane can be obtained by methods such as casting into a mold, spin-coating, doctor blading, extrusion, and the like. The membranes are stabilized through crosslinking with multivalent cations, preferably calcium. Optionally, the membranes can be further stabilized by substituting either alginate or hyaluronate with photo-reactive derivatives thereof that undergo chemical crosslinking when triggered by ultraviolet or visible light sources.

An embodiment of the invention is a method for using the aforementioned membrane to inhibit, reduce, or prevent scar tissue attachments. The membrane may be used in any anatomical location of the body for which there is a risk of scar tissue attachments. During a surgical procedure the membrane may be placed between two apposing organs or tissues. The membrane may be used in both open and minimally invasive surgical procedures.

An embodiment of the invention is a method of treating the aforementioned membrane with a stimulus, preferably a solution or gel, to modify the properties of the membrane. For example, the solution may enhance the tissue adherence of the membrane or increase the rate of membrane resorption within the body. Such a solution comprises a chelator (e.g., calcium chelator) that binds the multivalent cations stabilizing the membrane. The solution is applied during surgical procedures following insertion of the membrane into a person's body. Optionally, the solution may also comprise viscosity modifiers to facilitate surgical delivery.

An embodiment of the invention is the aforementioned membrane, comprising alginate and hyaluronate, with an entrapped pharmaceutically active ingredient. The active ingredient may be an antibiotic, anti-inflammatory, chemotherapeutic, anti-scarring, and/or pro-regenerative drug such as a growth factor or stem cell. In an embodiment the release of active ingredient from the membrane may be modified by the use of the aforementioned stimulus.

An embodiment of the invention is a bilayer hydrogel membrane comprising two distinct layers of which one inhibits, reduces, or prevents scar tissue attachments and the other layer promotes wound healing and regeneration. The two layers are joined through chemical, ionic, or physical bonds.

The following examples pertain to further embodiments.

Example 1 includes uncrosslinked hyaluronic acid and crosslinked alginate both included in a hydrogel film; and a calcium chelator; wherein (a) the alginate is crosslinked with calcium, (b) the hydrogel film is flat and includes a width, a length, and a thickness that is less than the width and the length, and (c) the hydrogel film is configured so bioresorbability of the hydrogel film increases in response to applying the calcium chelator to the hydrogel film.

In example 2 the subject matter of the Example 1 can optionally include wherein the calcium chelator is configured to disrupt calcium crosslinks within the hydrogel film.

In example 3 the subject matter of the Examples 1-2 can optionally include wherein the calcium chelator is selected from the group comprising citrate, EDTA, EGTA, and BAPTA.

In example 4 the subject matter of the Examples 1-3 can optionally include wherein concentration of the calcium chelator is 0.05 to 1.0 molar.

In example 5 the subject matter of the Examples 1-4 can optionally include a thickening agent.

In example 6 the subject matter of the Examples 1-5 can optionally include wherein the thickening agent includes sodium hyaluronate.

In example 7 the subject matter of the Examples 1-6 can optionally include wherein the thickening agent is configured to increase viscosity of the calcium chelator.

In example 8 the subject matter of the Examples 1-7 can optionally include wherein the hydrogel film consists essentially of hyaluronic acid and alginate.

In example 9 the subject matter of the Examples 1-8 can optionally include wherein the hydrogel film comprises at least 1% and no more than 33% composition hyaluronic acid.

In example 10 the subject matter of the Examples 1-9 can optionally include a first hydrogel layer comprising the uncrosslinked hyaluronic acid and the crosslinked alginate; and a second hydrogel layer comprising collagen and hyaluronic acid.

In example 11 the subject matter of the Examples 1-10 can optionally include wherein the first hydrogel layer is monolithic, the second hydrogel layer is monolithic but not monolithic with the first hydrogel layer, and the first and second hydrogel layers are covalently bound to one another.

In example 12 the subject matter of the Examples 1-11 can optionally include a third hydrogel layer comprising additional uncrosslinked hyaluronic acid and additional crosslinked alginate; wherein the third hydrogel layer is monolithic but not monolithic with the second hydrogel layer, the third and second hydrogel layers are covalently bound to one another, and the second hydrogel layer is between the first and third hydrogel layers.

In example 13 the subject matter of the Examples 1-12 can optionally include wherein the alginate is crosslinked around the uncrosslinked hyaluronic acid.

In example 14 the subject matter of the Examples 1-13 can optionally include wherein the hydrogel film comprises a therapeutic agent selected from the group comprising a drug, a pharmaceutical agent, a peptide, a protein, a medicine, a hormone, and a macromolecule.

In example 15 the subject matter of the Examples 1-14 can optionally include wherein the hydrogel film is configured so the hydrogel film's release rate for the therapeutic agent increases in response to applying the calcium chelator to the hydrogel film.

In example 16 the subject matter of the Examples 1-15 can optionally include wherein the alginate is crosslinked around the therapeutic agent.

In example 17 the subject matter of the Examples 1-16 can optionally include wherein the hydrogel film is configured so the hydrogel film's release rate for the therapeutic agent increases in response to increasing the amount of hyaluronate in the hydrogel film.

In example 18 the subject matter of the Examples 1-17 can optionally include a therapeutic agent selected from the group comprising a drug, a pharmaceutical agent, a peptide, a protein, a medicine, a hormone, and a macromolecule.

In example 19 the subject matter of the Examples 1-18 can optionally include wherein the hydrogel film is configured so mucoadhesiveness for the hydrogel film increases in response to applying the calcium chelator to the hydrogel film.

In example 20 the subject matter of the Examples 1-19 can optionally include wherein the hydrogel film is configured to increase in transparency in response to applying the calcium chelator to the hydrogel film.

In another embodiment the hydrogel film has a thickness of between 5 and 30 micrometers. However, in other embodiments the thickness is no greater than 5, 10, 15, 20, 25, 35, 40, 45, or 50 micrometers. In other embodiments the hydrogel film has a thickness of between 5 and 10, 10 and 15, 15 and 20, 20 and 25, 25 and 30, 30 and 40, 50 and 60, 70 and 80, 90 and 100 micrometers. In another embodiment the hydrogel film has a thickness not greater than 250 micrometers.

Example 21 includes a kit comprising: a hydrogel film consisting essentially of crosslinked alginate that is crosslinked around uncrosslinked hyaluronic acid to entrap the uncrosslinked hylalunonic acid within the crosslinked alginate; and a sequestering agent; wherein (a) the alginate is crosslinked with an ion, (b) the hydrogel film is planar, (c) the hydrogel film is configured so its bioresorbability increases in response to applying the sequestering agent to the hydrogel film, and (d) the sequestering agent is configured to sequester the ion.

In example 22 the subject matter of the Example 21 can optionally wherein the hydrogel film comprises: a first hydrogel layer comprising the uncrosslinked hyaluronic acid and the crosslinked alginate; and a second hydrogel layer comprising a therapeutic agent selected from the group comprising a drug, a pharmaceutical agent, a peptide, a protein, a medicine, a hormone, and a macromolecule; wherein (a) the first hydrogel layer is monolithic, (b) the second hydrogel layer is monolithic but not monolithic with the first hydrogel layer, (c) the first and second hydrogel layers are chemically bound to one another, (d) the second hydrogel layer is adhesive, and (e) the first hydrogel layer is anti-adhesive.

In example 23 the subject matter of the Examples 21-22 can optionally include wherein the hydrogel film includes a therapeutic agent selected from the group comprising a drug, a pharmaceutical agent, a peptide, a protein, a medicine, a hormone, and a macromolecule; and the hydrogel film is configured so its release rate for the therapeutic agent increases in response to applying the sequestering agent to the hydrogel film.

In example 24 the subject matter of the Examples 21-23 can optionally include wherein the hydrogel film is configured so mucoadhesiveness for the hydrogel film increases in response to applying the sequestering agent to the hydrogel film.

FIG. 6 includes a method in an embodiment.

Block 605 includes applying a hydrogel film to a subject, wherein the hydrogel film includes uncrosslinked hyaluronic acid and crosslinked alginate, and the alginate is crosslinked with calcium.

Block 610 includes applying a calcium chelator to the hydrogel to (a) increase bioresorbability of the hydrogel film in response to applying the calcium chelator to the hydrogel film, (b) tune the hydrogel film's release rate for a therapeutic agent included in the hydrogel by applying the calcium chelator to the hydrogel film, and/or (c) increasing the mucoadhesiveness for the hydrogel film by applying the calcium chelator to the hydrogel film. Block 610 may occur once or repeatedly. For example, the chelator may be added immediately after the hydrogel is applied to the patient. In addition, the chelator may be added again several hours, days, or weeks after the initial chelator application. In addition, the initial chelator application may occur hours, days, or weeks after the hydrogel is applied to the patient.

Block 607 is optional. Block 607 includes applying a thickening agent to the calcium chelator to increase viscosity of the calcium chelator. This may be done before or after the calcium chelator is applied to the hydrogel.

In an embodiment the hydrogel film includes a first hydrogel layer comprising the uncrosslinked hyaluronic acid and the crosslinked alginate; and a second hydrogel layer comprising collagen and hyaluronic acid. With such an embodiment block 605 may include applying the second hydrogel layer to a wound of the patient.

In an embodiment the calcium chelator addressed in FIG. 6 is replaced with sequestering agent and the calcium crosslinked is more generally based on crosslinking based on an ion corresponding to the sequestering agent.

Another embodiment includes a method comprising applying a hydrogel film to a subject, wherein the hydrogel film includes uncrosslinked hyaluronic acid and crosslinked alginate. The alginate is crosslinked with calcium, and the hydrogel film is flat and includes a width, a length, and a thickness that is less than the width and the length. The method further comprises applying a calcium chelator to the hydrogel to increase bioresorbability of the hydrogel film in response to applying the calcium chelator to the hydrogel film. The method further comprises applying a calcium chelator to the hydrogel more than 1 day after applying the hydrogel to the patient. In an embodiment the method further comprises applying a thickening agent to the calcium chelator to increase viscosity of the calcium chelator. In an embodiment the hydrogel film includes a first hydrogel layer comprising the uncrosslinked hyaluronic acid and the crosslinked alginate; and a second hydrogel layer comprising collagen and hyaluronic acid. The method further comprises applying second hydrogel layer to a wound of the patient. Another embodiment includes rolling the hydrogel film into a roll whose outer surface includes the first hydrogel layer. The embodiment includes contacting the first hyrogel layer with trocar, introducer, or tube to introduce the hydrogel film into the patient without having the hydrogel film stick or adhere to the trocar, introducer, or tube. In an embodiment the hydrogel film comprises a therapeutic agent selected from the group comprising a drug, a pharmaceutical agent, a peptide, a protein, a medicine, a hormone, and a macromolecule. The method may comprise tuning the hydrogel film's release rate for the therapeutic agent by applying the calcium chelator to the hydrogel film. In an embodiment the method may comprise increasing the mucoadhesiveness for the hydrogel film by applying the calcium chelator to the hydrogel film.

Another embodiment includes a method comprising applying a hydrogel film to a subject, wherein the hydrogel film includes uncrosslinked hyaluronic acid and crosslinked alginate. The alginate is crosslinked with an ion, and the hydrogel film is flat and includes a width, a length, and a thickness that is less than the width and the length. The method further comprises applying a sequestering agent to the hydrogel to increase bioresorbability of the hydrogel film in response to applying the sequestering agent to the hydrogel film. In an embodiment the method further comprises applying a thickening agent to the sequestering agent to increase viscosity of the sequestering agent. In an embodiment the hydrogel film includes a first hydrogel layer comprising the uncrosslinked hyaluronic acid and the crosslinked alginate; and a second hydrogel layer a therapeutic agent. The method further comprises applying second hydrogel layer to a wound of the patient. Another embodiment includes rolling the hydrogel film into a roll whose outer surface includes the first hydrogel layer. The embodiment includes contacting the first hydrogel layer with trocar, introducer, or tube to introduce the hydrogel film into the patient without having the hydrogel film stick or adhere to the trocar, introducer, or tube. In an embodiment the hydrogel film comprises a therapeutic agent selected from the group comprising a drug, a pharmaceutical agent, a peptide, a protein, a medicine, a hormone, and a macromolecule. The method may comprise tuning the hydrogel film's release rate for the therapeutic agent by applying the sequestering agent to the hydrogel film. In an embodiment the method may comprise increasing the mucoadhesiveness for the hydrogel film by applying the sequestering agent to the hydrogel film.

Another embodiment includes no kit but instead just includes a hydrogel. Such an embodiment includes uncrosslinked hyaluronic acid and crosslinked alginate both included in a hydrogel film; wherein (a) the alginate is crosslinked with calcium, (b) the hydrogel film is flat and includes a width, a length, and a thickness that is less than the width and the length, and (c) the hydrogel film is configured so bioresorbability of the hydrogel film increases in response to applying a calcium chelator to the hydrogel film. Such a calcium chelator would be configured to disrupt calcium crosslinks within the hydrogel film. In an embodiment the hydrogel film consists essentially of hyaluronic acid and alginate. In an embodiment the hydrogel film comprises at least 1% and no more than 33% composition hyaluronic acid. In an embodiment the hydrogel film comprises: a first hydrogel layer comprising the uncrosslinked hyaluronic acid and the crosslinked alginate; and a second hydrogel layer comprising collagen and hyaluronic acid. In an embodiment the first hydrogel layer is monolithic, the second hydrogel layer is monolithic but not monolithic with the first hydrogel layer, and the first and second hydrogel layers are covalently bound to one another. In an embodiment the hydrogel film comprises: a third hydrogel layer comprising additional uncrosslinked hyaluronic acid and additional crosslinked alginate; wherein the third hydrogel layer is monolithic but not monolithic with the second hydrogel layer, the third and second hydrogel layers are covalently bound to one another, and the second hydrogel layer is between the first and third hydrogel layers. In an embodiment the alginate is crosslinked around the uncrosslinked hyaluronic acid. In an embodiment the hydrogel film comprises a therapeutic agent selected from the group comprising a drug, a pharmaceutical agent, a peptide, a protein, a medicine, a hormone, and a macromolecule. In an embodiment the hydrogel film is configured so the hydrogel film's release rate for the therapeutic agent increases in response to applying the calcium chelator to the hydrogel film. In an embodiment the alginate is crosslinked around the therapeutic agent. In an embodiment the hydrogel film is configured so the hydrogel film's release rate for the therapeutic agent increases in response to increasing the amount of hyaluronate in the hydrogel film. In an embodiment the hydrogel film is configured so mucoadhesiveness for the hydrogel film increases in response to applying the calcium chelator to the hydrogel film. In an embodiment the hydrogel film is configured to increase in transparency in response to applying the calcium chelator to the hydrogel film. In an embodiment the hydrogel film has a thickness of between 5 and 30 micrometers. In an embodiment the calcium chelator addressed in this paragraph is replaced with sequestering agent and the calcium crosslinked is more generally based on crosslinking based on an ion corresponding to the sequestering agent.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A kit comprising:
uncrosslinked hyaluronic acid and crosslinked alginate both included in a hydrogel film; and a calcium chelator;

wherein (a) the alginate is crosslinked with calcium, (b) the hydrogel film is flat and includes a width, a length, and a thickness that is less than the width and the length, (c) the hydrogel film is configured so bioresorbability of the hydrogel film increases in response to applying the calcium chelator to the hydrogel film, and (d) the hydrogel film is not templated by a crystal.

2. A system comprising:

uncrosslinked hyaluronic acid and crosslinked alginate both included in a hydrogel; and a calcium chelator;

wherein (a) the alginate is crosslinked with calcium, (b) the hydrogel is configured so bioresorbability of the hydrogel increases in response to applying the calcium chelator to the hydrogel, (c) the hydrogel is configured to leach the hyaluronic acid, and (d) the hydrogel is not templated by a crystal.

3. The system of claim 2, wherein the calcium chelator includes at least one of citrate, EDTA, EGTA, BAPTA, a phosphate, or combinations thereof.

4. The system of claim 2, wherein the hydrogel comprises:
   a first hydrogel layer comprising the uncrosslinked hyaluronic acid and the crosslinked alginate; and
   a second hydrogel layer comprising collagen and additional hyaluronic acid.

5. The system of claim 3 wherein the hydrogel comprises a therapeutic agent that includes at least one of a drug, a pharmaceutical agent, a peptide, a protein, a medicine, a hormone, a macromolecule, or combinations thereof.

6. The system of claim 5, wherein the hydrogel is configured so the hydrogel's release rate of the therapeutic agent increases in response to applying the calcium chelator to the hydrogel.

7. The system of claim 6, wherein the hydrogel is configured so the hydrogel's release rate for the therapeutic agent increases in response to increasing an amount of hyaluronate in the hydrogel.

8. The system of claim 7, wherein the hydrogel is configured so mucoadhesiveness for the hydrogel increases in response to applying the calcium chelator to the hydrogel.

9. The system of claim 8, wherein the hydrogel is configured to increase in transparency in response to applying the calcium chelator to the hydrogel.

10. The system of claim 2 including a sealed package that includes the hydrogel and the calcium chelator.

11. A system comprising:

uncrosslinked hyaluronic acid and crosslinked alginate both included in a hydrogel;

a sequestering agent;

wherein (a) the alginate is crosslinked with a multivalent cation, (b) the hydrogel is configured so its bioresorbability increases in response to applying the sequestering agent to the hydrogel, (c) the sequestering agent is configured to sequester the multivalent cation, (d) the hydrogel is configured to leach the hyaluronic acid, and (e) the hydrogel is not templated by a crystal.

12. The system of claim 11, wherein:

the hydrogel comprises a therapeutic agent that includes at least one of a drug, a pharmaceutical agent, a peptide, a protein, a medicine, a hormone, a macromolecule, or combinations thereof;

the hydrogel is configured so a release rate for the therapeutic agent increases in response to applying the sequestering agent to the hydrogel.

13. The system of claim 12 wherein:

the hydrogel is configured so mucoadhesiveness of the hydrogel increases in response to applying the sequestering agent to the hydrogel;

the hydrogel is configured to increase in transparency in response to applying the sequestering agent to the hydrogel.

14. The system of claim 13 including a sealed package that includes the hydrogel and the sequestering agent.

15. The system of claim 11 wherein the hydrogel consists essentially of the uncrosslinked hyaluronic acid and the crosslinked alginate.

16. The system of claim 11 wherein the hyaluronic acid is entrapped within a non-templated pore of the hydrogel based on the hyaluronic acid's size as compared to the non-templated pore's size.

17. The system of claim 16 wherein the hydrogel is configured to leach the hyaluronic acid in response to exposing the hydrogel to water.

18. The system of claim 17 wherein the hydrogel is configured to leach the hyaluronic acid in response to exposing the hydrogel to water in vivo.

19. The system of claim 17 wherein:

the hydrogel is configured to leach the hyaluronic acid at a rate;

the rate is based on a ratio of the hyaluronic acid to the alginate;

in rate increases as the ratio increases.

* * * * *